(12) United States Patent
Knapp

(10) Patent No.: US 11,737,759 B2
(45) Date of Patent: Aug. 29, 2023

(54) SURGICAL STAPLING DEVICE ACCOMMODATING PROLAPSED TISSUE

(71) Applicant: Covidien LP, Mansfield, MA (US)

(72) Inventor: Robert H. Knapp, Middlebury, CT (US)

(73) Assignee: Covidien LP, Mansfield, MA (US)

( * ) Notice: Subject to any disclaimer, the term of this patent is extended or adjusted under 35 U.S.C. 154(b) by 182 days.

(21) Appl. No.: 17/394,789

(22) Filed: Aug. 5, 2021

(65) Prior Publication Data

US 2023/0041791 A1    Feb. 9, 2023

(51) Int. Cl.
    *A61B 17/11*       (2006.01)
    *A61B 17/115*     (2006.01)

(52) U.S. Cl.
    CPC ....... *A61B 17/1155* (2013.01); *A61B 17/1114* (2013.01)

(58) Field of Classification Search
    CPC .................................................. A61B 17/1155
    See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

International Search Report and Written Opinion dated Nov. 2, 2022, issued in corresponding international application No. PCT/IB2022/057201, 12 pages.

*Primary Examiner* — Praachi M Pathak
(74) *Attorney, Agent, or Firm* — Carter, DeLuca & Farrell LLP

(57) ABSTRACT

A surgical stapling device includes an end effector configured to accommodate prolapsed tissue to perform an anastomosis externally of a body cavity. The surgical stapling device has an anvil assembly and a shell assembly. The anvil assembly includes an anvil plate and anvil rods that extend proximally from the anvil shaft and are positioned about the shell assembly. The anvil plate has a proximally facing surface that defines staple forming pockets. The shell assembly includes a shell housing that defines a cavity, an annular pusher that is movable within the cavity from a retracted position to an advanced position, an annular staple cartridge, and an annular knife blade. The staple cartridge includes staple receiving pockets that receive staples, and the knife blade is secured to the pusher radially outwardly of the staple receiving pockets.

20 Claims, 11 Drawing Sheets

(56) References Cited

U.S. PATENT DOCUMENTS

| | | |
|---|---|---|
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |

(56) References Cited

U.S. PATENT DOCUMENTS

| | | |
|---|---|---|
| 6,488,197 B1 | 12/2002 | Whitman |
| 6,491,201 B1 | 12/2002 | Whitman |
| 6,494,877 B2 | 12/2002 | Dell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |

(56) References Cited

U.S. PATENT DOCUMENTS

| | | |
|---|---|---|
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |
| 9,351,729 B2 | 5/2016 | Orban, III et al. |
| 9,351,731 B2 | 5/2016 | Carter et al. |
| 9,364,229 B2 | 6/2016 | D'Agostino et al. |
| 9,370,366 B2 | 6/2016 | Mozdzierz |
| 9,370,367 B2 | 6/2016 | Mozdzierz |
| 9,393,014 B2 | 7/2016 | Milliman |

(56) References Cited

U.S. PATENT DOCUMENTS

| | | |
|---|---|---|
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,898,196 B2 | 1/2021 | Sapienza et al. |
| 2003/0111507 A1 | 6/2003 | Nunez |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0042443 A1* | 2/2011 | Milliman ............ A61B 17/115 227/176.1 |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0234890 A1 | 9/2012 | Aronhalt et al. |
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |
| 2013/0200131 A1 | 8/2013 | Racenet et al. |
| 2013/0206816 A1 | 8/2013 | Penna |
| 2013/0240597 A1 | 9/2013 | Milliman et al. |
| 2013/0277411 A1 | 10/2013 | Hodgkinson et al. |
| 2013/0284792 A1 | 10/2013 | Ma |
| 2014/0008413 A1 | 1/2014 | Williams |
| 2014/0046352 A1 | 2/2014 | Reboa et al. |
| 2014/0158747 A1 | 6/2014 | Measamer et al. |
| 2014/0284370 A1 | 9/2014 | Sahin |
| 2015/0083772 A1 | 3/2015 | Miller et al. |
| 2015/0173763 A1 | 6/2015 | Liu |

(56) References Cited

U.S. PATENT DOCUMENTS

2015/0209045 A1 7/2015 Hodgkinson et al.
2020/0315627 A1* 10/2020 Guerrera ............ A61B 17/1155

FOREIGN PATENT DOCUMENTS

| | | |
|---|---|---|
| CN | 104039244 A | 9/2014 |
| CN | 104042288 A | 9/2014 |
| CN | 104367360 A | 2/2015 |
| CN | 106214204 B | 7/2018 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1671597 A1 | 6/2006 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3023077 A1 | 5/2016 |
| EP | 3649964 A1 | 5/2020 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 02080781 A2 | 10/2002 |
| WO | 2004047654 A2 | 6/2004 |
| WO | 2008107918 A1 | 9/2008 |
| WO | 2019130087 A1 | 7/2019 |

* cited by examiner

SURGICAL STAPLING DEVICE ACCOMMODATING PROLAPSED TISSUE

FIELD

The disclosure relates generally to surgical stapling devices, and more particularly to surgical stapling devices for performing anastomosis of prolapsed tissue.

BACKGROUND

Anastomosis is the surgical joining of separate hollow organ sections. Typically, an anastomosis procedure follows surgery in which a diseased or defective section of hollow tissue is removed, and the end sections are occluded or sealed (e.g., stapled via a linear surgical stapler). Depending on the desired anastomosis procedure, the end sections may be joined by using either circular, end-to-end, or side-to-side organ reconstruction methods.

Certain anastomosis procedures are performed on portions of tissue that are challenging to access. Likewise, it may be challenging to cut, occlude, and/or seal the end sections of tissue prior to the joining of tissue. For instance, lower anterior resection (LAR) procedures generally involve sealing and segmentation of the lower colon/rectum. The narrow pelvic structure makes it difficult to position traditional linear stapling devices in the desired location. Further, the geometry of non-linear stapling and cutting instruments often requires the surgical device to be non-laparoscopic.

One problem associated with anastomosis procedures, and particularly LAR procedures, is anastomotic leakage. To minimize any likelihood of anastomotic leakage, a temporary stoma may be created to allow the anatomized tissue to heal. However, stomas can be problematic and require a patient to wear a colostomy bag. The colostomy bag can lead to infection due to exposure of internal organs to the outside environment. Depending on how the resection heals, stomas may be permanent.

A continuing need exists in the art for a surgical device that can reduce the need for stoma creation.

SUMMARY

Aspects of the disclosure are directed to a surgical stapling device that is configured to perform an anastomosis on prolapsed tissue externally of a body cavity. The surgical stapling device includes an end effector that has an anvil assembly and a shell assembly. The anvil assembly includes an anvil plate and anvil rods that extend proximally from the anvil shaft and are positioned about the shell assembly. The anvil plate has a proximally facing surface that defines staple forming pockets. The shell assembly includes a shell housing that defines a cavity, an annular pusher that is movable within the cavity from a retracted position to an advanced position, an annular staple cartridge, and an annular knife blade. The staple cartridge includes staple receiving pockets that receive staples, and the knife blade is secured to the pusher radially outwardly of the staple receiving pockets.

Aspects of this disclosure are directed to a surgical stapling device that includes a handle assembly, an elongate body, and an end effector. The handle assembly includes a firing trigger and an approximation knob. The elongate body has a proximal portion and a distal portion, and the proximal portion is coupled to the handle assembly. The end effector is coupled to the distal portion of the elongate body and includes an anvil assembly and a shell assembly. The anvil assembly includes an anvil plate and anvil rods that extend proximally from the anvil plate and are positioned about the shell assembly. The anvil plate has a proximally facing surface that defines staple forming pockets. The shell assembly includes a shell housing that defines a cavity, an annular pusher that is movable within the cavity from a retracted position to an advanced position, an annular staple cartridge, and an annular knife blade. The staple cartridge includes staple receiving pockets that receive staples, and the knife blade is secured to the pusher radially outwardly of the staple receiving pockets.

Other aspects of the disclosure are directed to an end effector that includes an anvil assembly and a shell assembly. The anvil assembly includes an anvil plate and anvil rods that extend proximally from the anvil plate. The anvil plate has a proximally facing surface that defines staple forming pockets. The shell assembly includes a shell housing that defines a cavity, an annular pusher that is movable within the cavity from a retracted position to an advanced position, an annular staple cartridge, and an annular knife blade. The staple cartridge defines staple receiving pockets that receive staples, and the knife blade is secured to the pusher radially outwardly of the staple receiving pockets. The anvil rods are positioned about the shell assembly.

Still other aspects of the disclosure are directed to a surgical stapling device that includes an elongate body and an end effector. The elongate body has a proximal portion and a distal portion. The end effector is coupled to the distal portion of the elongate body and includes an anvil assembly and a shell assembly. The anvil assembly includes an anvil plate and anvil rods that extend proximally from the anvil plate and are positioned about the shell assembly. The anvil plate has a proximally facing surface that defines staple forming pockets. The shell assembly includes a shell housing that defines a cavity, an annular pusher that is movable within the cavity from a retracted position to an advanced position, an annular staple cartridge, and an annular knife blade. The staple cartridge includes staple receiving pockets that receive staples, and the knife blade is secured to the pusher radially outwardly of the staple receiving pockets. The shell assembly includes a centering cone that is received within the cavity of the shell housing and extends distally of the staple cartridge.

In aspects of the disclosure, the anvil plate has an annular configuration and defines an opening.

In some aspects of the disclosure, the shell assembly includes a centering cone that is received within the cavity of the shell housing and extends distally of the staple cartridge.

In certain aspects of the disclosure, the centering cone has a blunt distal end.

In aspects of the disclosure, the annular pusher includes fingers that are received within the staple receiving pockets of the staple cartridge such that movement of the annular pusher ejects the staples from the staple receiving pockets.

In aspects of the disclosure, the anvil assembly includes four anvil rods.

In some aspects of the disclosure, the anvil rods are spaced evenly about the anvil plate.

Other features of the disclosure will be appreciated from the following description.

DESCRIPTION OF THE DRAWINGS

Various aspects of the disclosure are illustrated herein with reference to the accompanying drawings, wherein.

DETAILED DESCRIPTION

Figure 1:
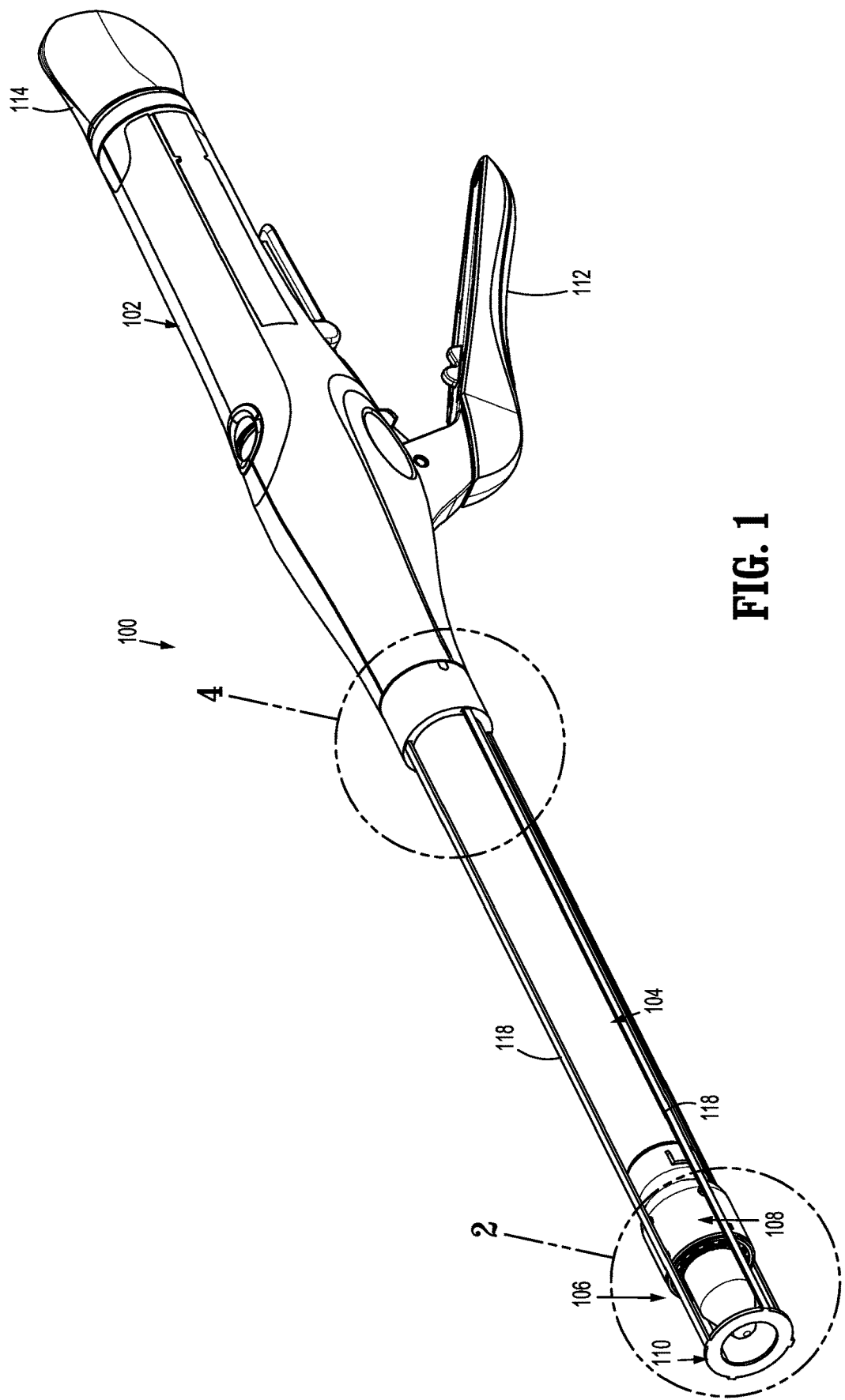
FIG. 1 is a side perspective view of a surgical stapling device according to aspects of the disclosure with an anvil assembly in an open or unclamped position.

The disclosed surgical stapling device will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician during use of the device in its customary manner, while the term "distal" is used generally to refer to that portion of the device that is farther from the clinician during use of the device in its customary manner. In addition, the term "clinician" is used generally to refer to medical personnel including doctors, nurses, and support personnel. Further, directional terms such as front, rear, upper, lower, top, bottom, and similar terms are used to assist in understanding the description and are not intended to limit the disclosure.

The disclosure is directed to a surgical stapling device that is configured to accommodate prolapsed tissue to perform an anastomosis externally of a body of a patient. In aspects of the disclosure, the surgical stapling device includes an end effector that includes an anvil assembly and a shell assembly. The anvil assembly includes an anvil plate and anvil rods that extend proximally from the anvil shaft and are positioned about the shell assembly. The anvil plate has a proximally facing surface that defines staple forming pockets. The shell assembly includes a shell housing that defines a cavity, an annular pusher that is movable within the cavity from a retracted position to an advanced position, an annular staple cartridge, and an annular knife blade. The staple cartridge includes staple receiving pockets that receive staples, and the knife blade is secured to the pusher radially outwardly of the staple receiving pockets.

FIG. 1 illustrates a surgical stapling device shown generally as stapling device 100 according to aspects of the disclosure. The stapling device 100 includes a handle assembly or actuator 102, an elongate body 104 that extends distally from the handle assembly 102, and an end effector 106 that includes a shell assembly 108 and an anvil assembly 110. The handle assembly 102 includes a firing trigger 112 and a rotatable approximation knob 114. Although shown as being a manually actuable handle assembly 102, the handle assembly may be a powered handle assembly. U.S. Pat. No. 7,303,106 and U.S. Patent Publication No. 2014/0263556 disclose examples of surgical stapling devices including manually actuated and powered handle assemblies. It is also envisioned that the disclosed aspects of this disclosure are suitable for use with robotically controlled surgical systems.

Figure 7:
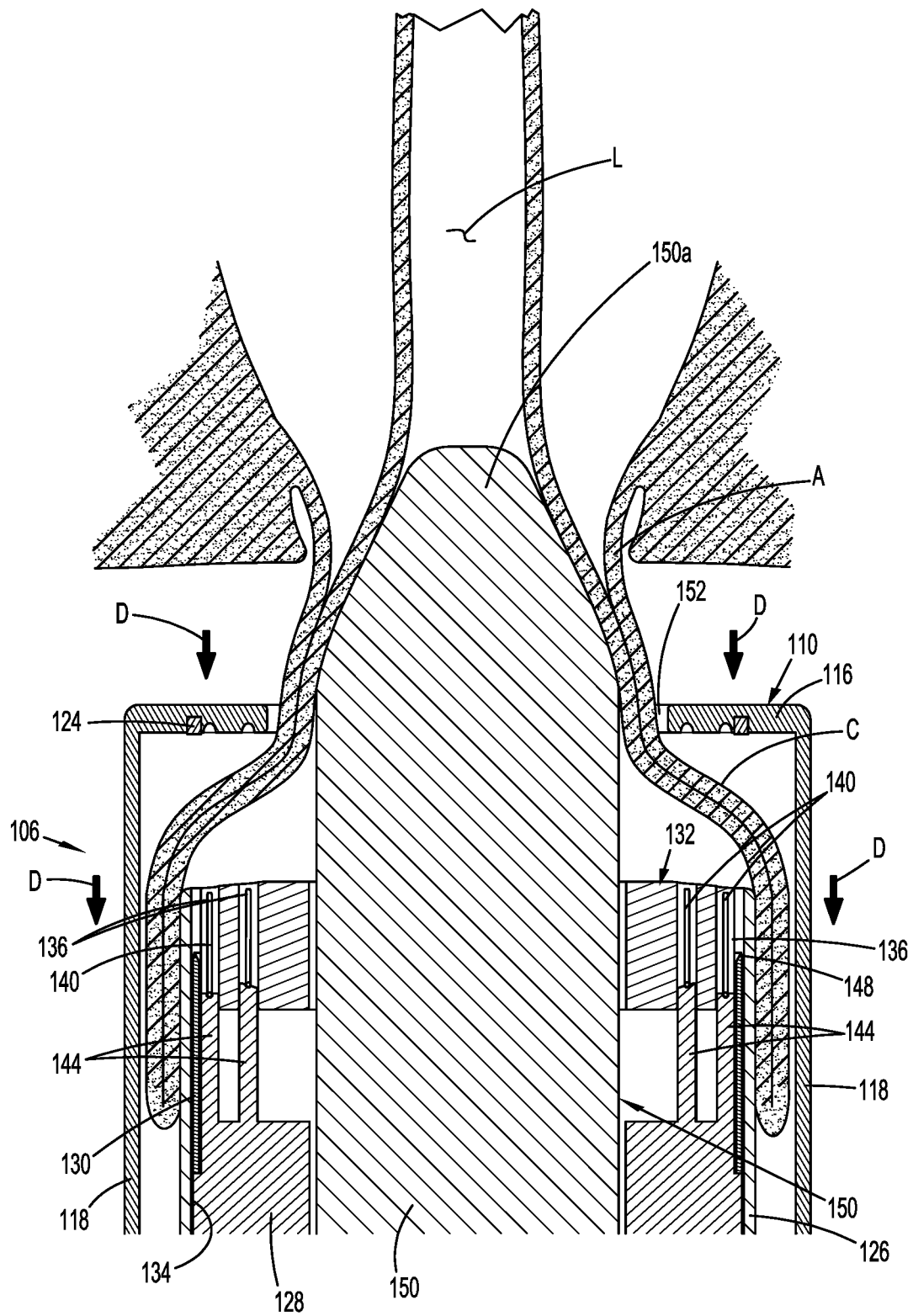
FIG. 7 is a cross-sectional view taken through the end effector shown in FIG. 6 as the anvil assembly is moved towards the clamped position.

FIGS. 2-5 illustrate the end effector 106 of the stapling device 100 (FIG. 1) which includes the shell assembly 108 and the anvil assembly 110. The anvil assembly 110 includes an anvil plate 116 and anvil rods 118. The anvil plate 116 has an annular configuration and includes a proximally facing surface 120 (FIG. 3) that defines staple forming pockets 122 and supports an annular cut ring 124 (FIG. 7). In aspects of the disclosure, the staple forming pockets 122 are arranged in one or more circular rings, e.g., three rings, that are positioned about the annular plate 116. Each of the anvil rods 118 has distal portion that is secured to or integrally formed with the anvil plate 116 and a proximal portion that extends into the handle assembly 12. In aspects of the disclosure, the anvil rods 118 are spaced evenly about the anvil plate 116. In some aspects of the disclosure, the anvil assembly 110 includes four anvil rods 118 spaced ninety-degrees apart about the anvil plate 116. Although the anvil rods 118 are shown to have rectangular cross-sectional configurations, it is envisioned that the anvil rods 118 could have a variety of different configurations including, e.g., circular, elliptical, and square. Although not shown, the anvil rods 118 are coupled to the approximation knob 114 via an approximation mechanism such that actuation of the approximation knob 114 causes the anvil plate 116 to move in relation to the shell assembly 108 between open and clamped positions.

Figure 2:
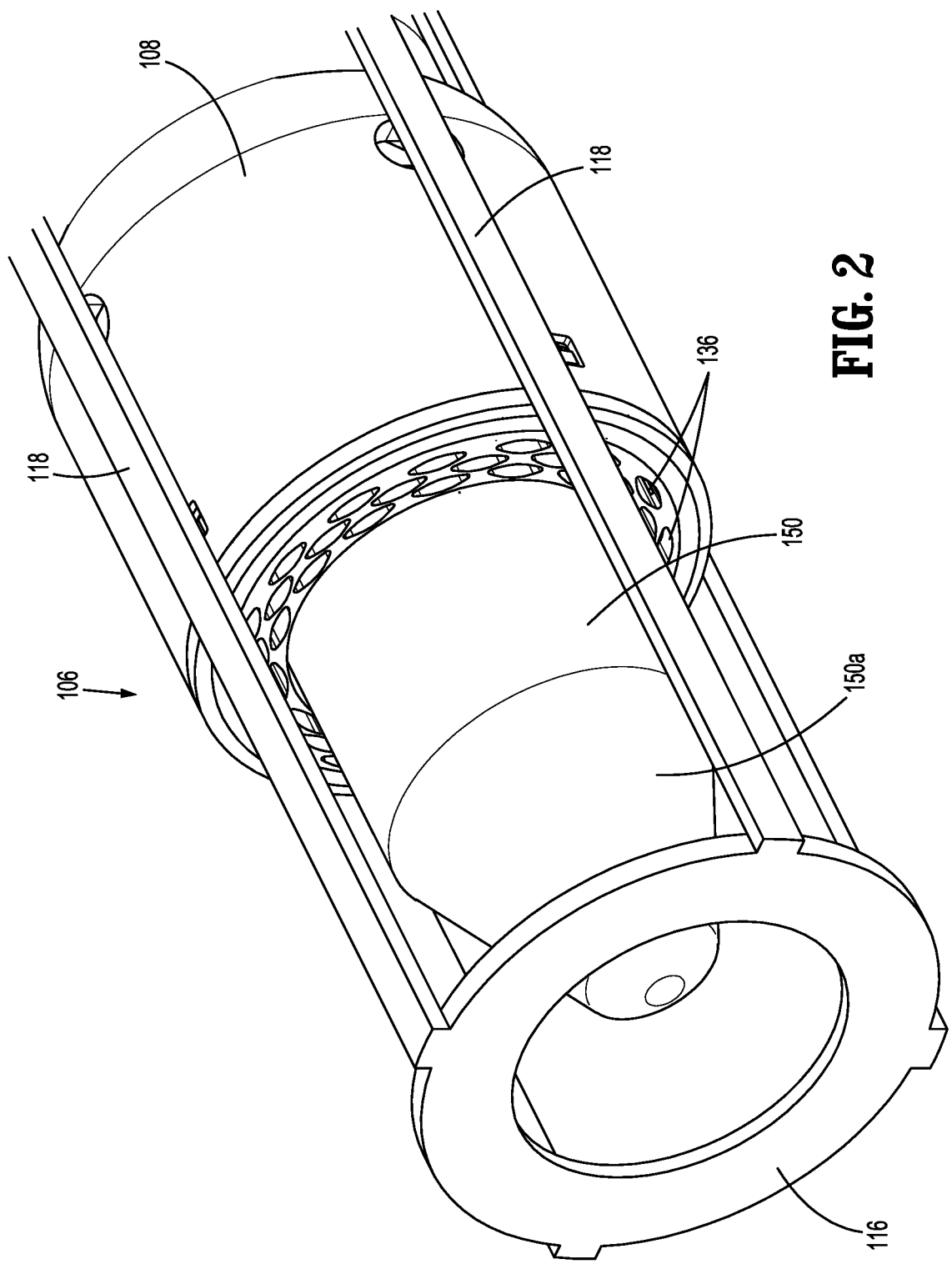
FIG. 2 is an enlarged view of the indicated area of detail shown in FIG. 1.
Figure 3:
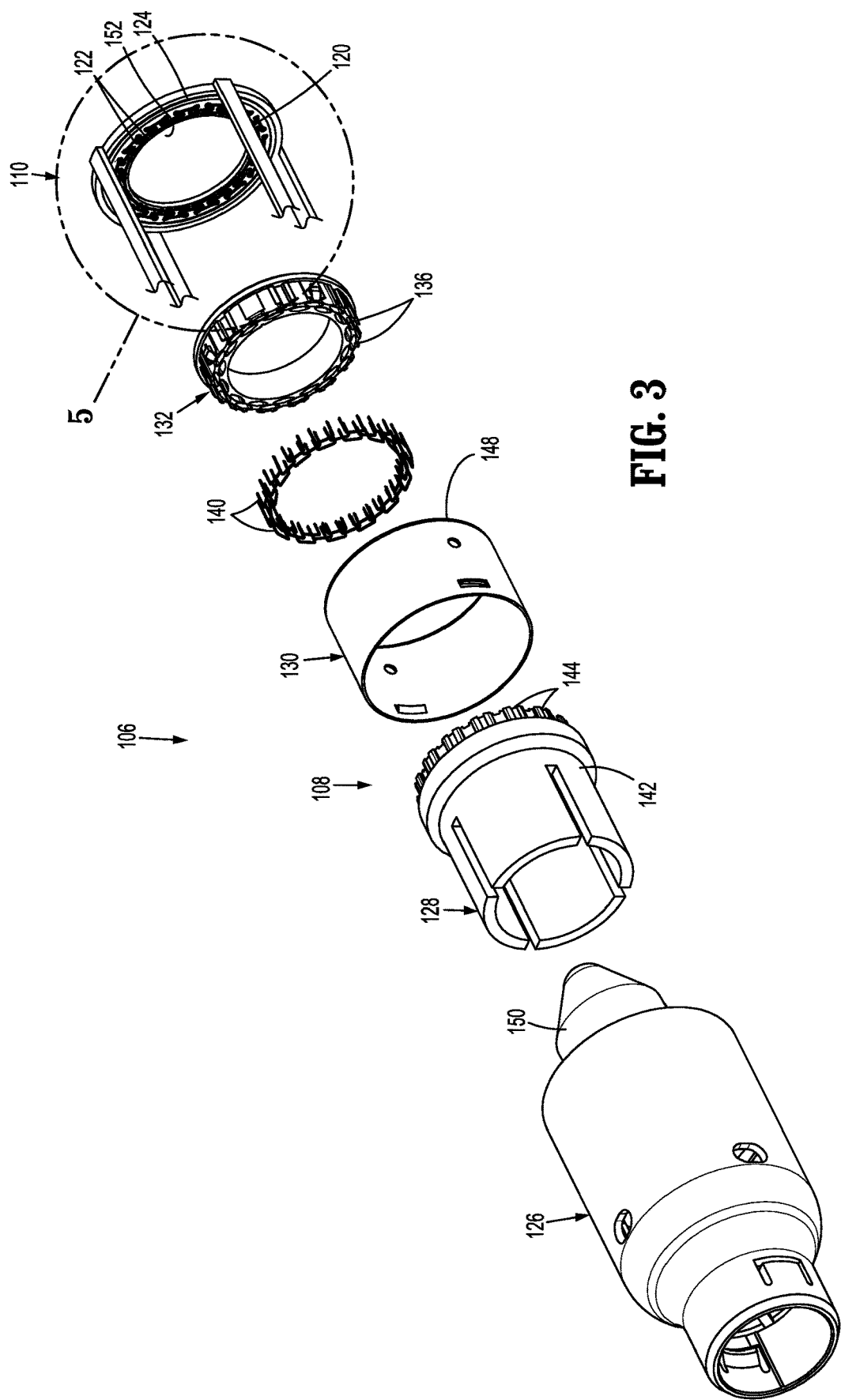
FIG. 3 is an exploded perspective view of an end effector of the surgical stapling device shown in FIG. 1 including the anvil assembly and a shell assembly.
Figure 4:
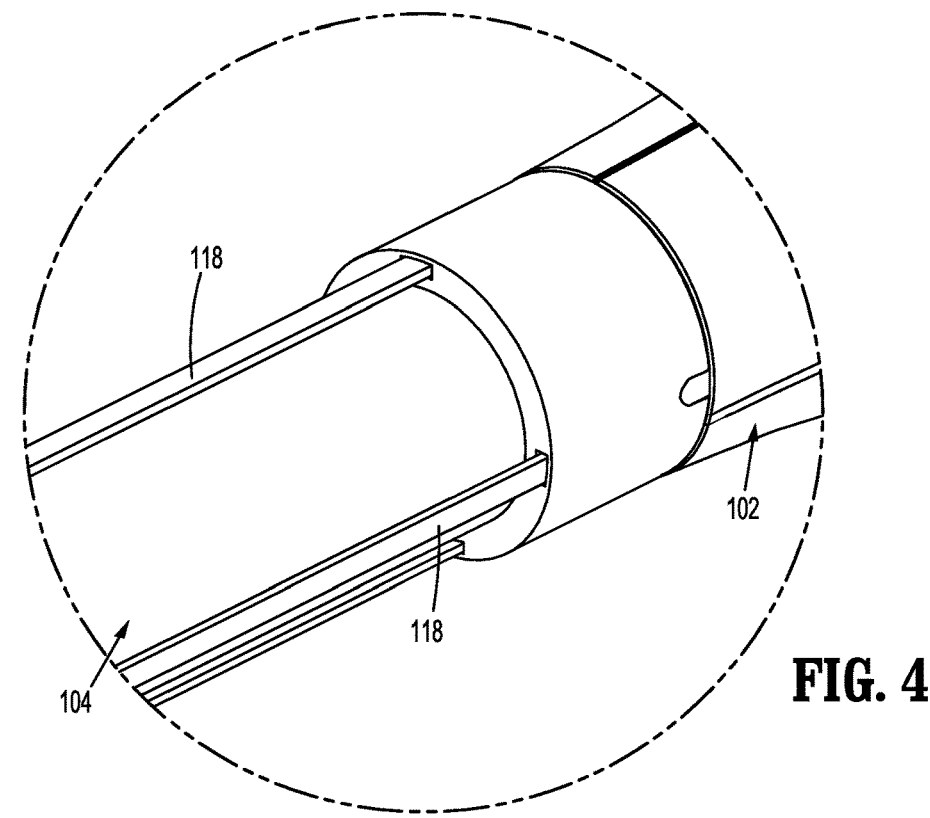
FIG. 4 is an enlarged view of the indicated area of detail shown in FIG. 1.
Figure 5:
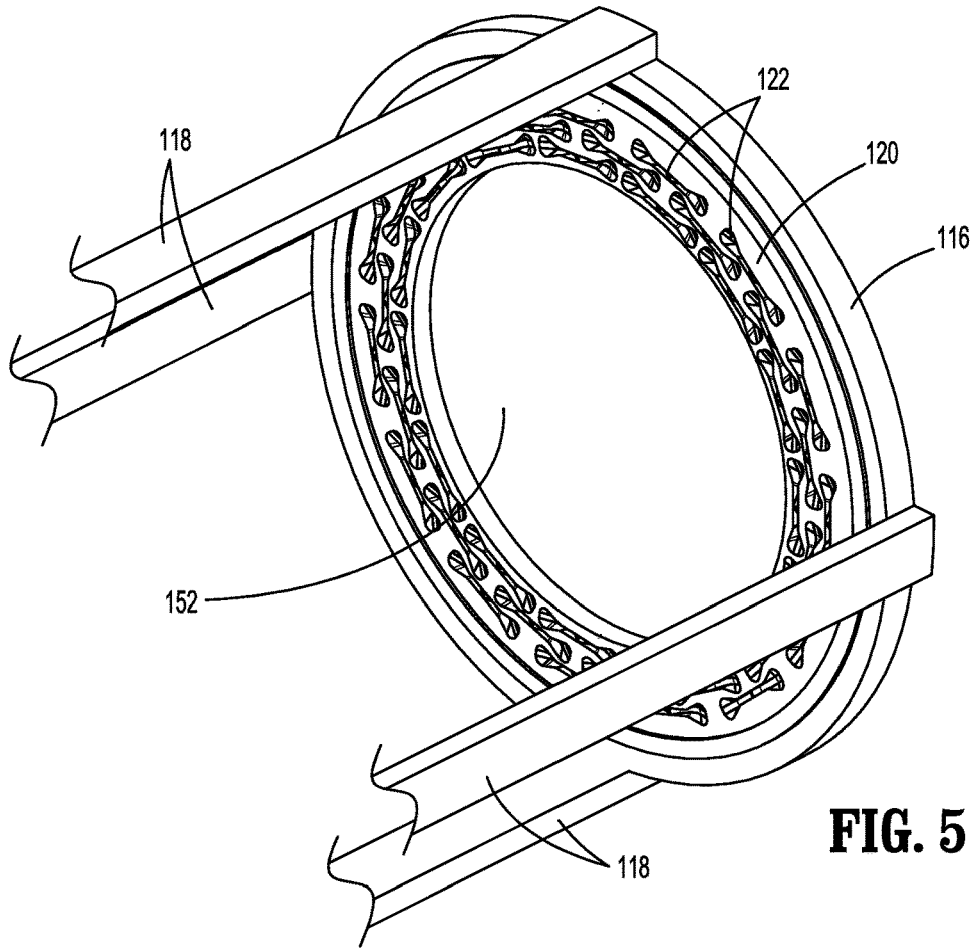
FIG. 5 is an enlarged view of the indicated area of detail shown in FIG. 3.

FIGS. 2 and 3 illustrate the shell assembly 108 which includes a shell housing 126, a pusher 128, a knife blade 130, and a staple cartridge 132. The shell housing 126 is coupled to a distal portion of the elongate body 104 of the stapling device 100 (FIG. 1) and defines a cylindrical cavity 134 (FIG. 7). The staple cartridge 132 is secured to a distal portion of the shell housing 126 and defines staple receiving pockets 136. In aspects of the disclosure, the staple receiving pockets 136 are arranged in one or more circular rings, e.g., three rings, that are positioned about the staple cartridge 132. Each of the staple receiving pockets 136 is aligned with a respective one of the staple forming pockets 122 in the anvil plate 116 and receives a staple 140.

The pusher 128 is received in the cylindrical cavity 134 (FIG. 7) of the shell housing 126 and includes a substantially cylindrical body 142 and fingers 144 that extend distally from the cylindrical body 142. Each of the fingers 144 is received within one of the staple receiving pockets 136 of the staple cartridge 132 and engages a staple 140. The pusher 128 is movable from a retracted position to an advanced position in response to actuation of the firing trigger 112 to eject the staples 140 from the staple receiving pockets 136 into the staple forming pockets 122 of the anvil plate 122 to form the staples 140 against the anvil plate 116 of the anvil assembly 110.

The knife blade 130 has an annular configuration and has a proximal portion that is fixedly secured to an outer surface of a distal portion of the pusher 128. The knife blade 130 has a distal portion that includes an annular cutting edge 148 that is positioned proximally of the distal portions of the staples 140 when the pusher 128 is in its retracted position. The cutting edge 148 of the knife blade 130 is positioned radially outward of the staples 140. When the stapling device 100 (FIG. 1) is fired by actuating the firing trigger 112 (FIG. 1), the staples 140 engage tissue before the cutting edge 148 of the knife blade 130 cuts tissue. Although not shown, the staple cartridge 132 can be secured to an internal portion of the shell housing 126 to allow the knife blade 130 to pass entirely about the staple cartridge 132 radially outward of the staples 140.

The shell assembly 108 also includes a centering cone 150 that is fixedly received within the cylindrical cavity 134 (FIG. 7) of the shell housing 126 and extends through an opening of the pusher 128 and through an opening of the staple cartridge 132. The centering cone 150 extends from the shell housing 126 to a position distally of the shell housing 126. In aspects of the disclosure, the centering cone 150 has a tapered, blunt distal end 150a (FIG. 2) that is configured to be atraumatically inserted into a lumen of a vessel, e.g., the colon.

Figure 6:
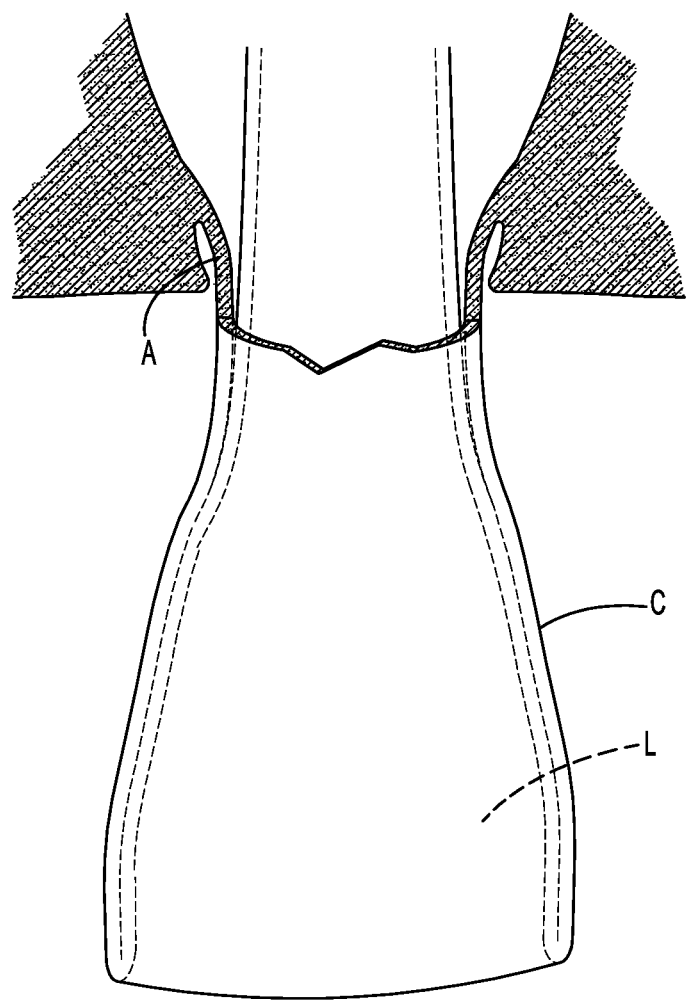
FIG. 6 is a cross-sectional view taken through prolapsed tissue of a patient.
Figure 6A:
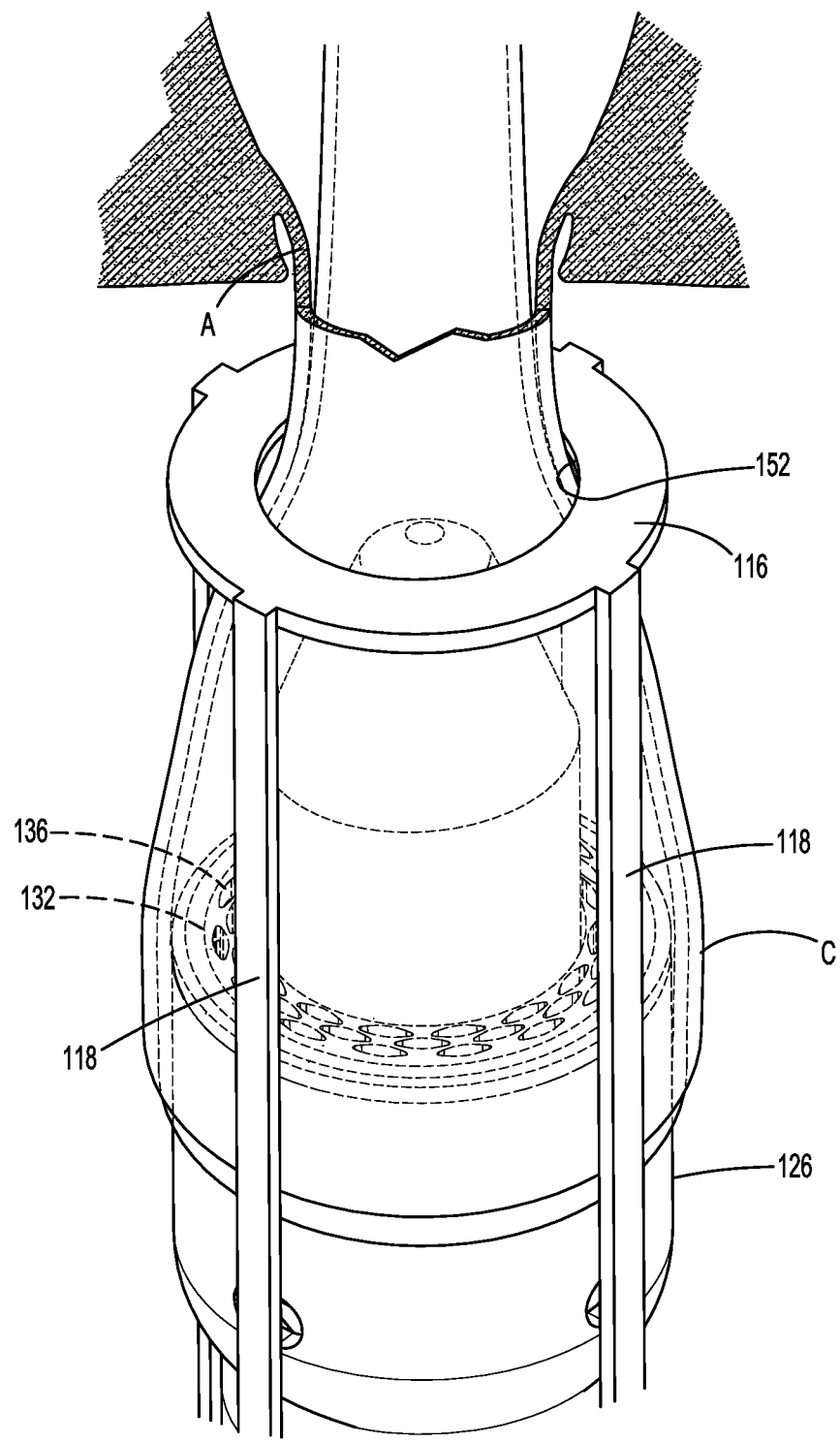
FIG. 6A is a side perspective view of the end effector of the surgical stapling device shown in FIG. 1 in the open position with prolapsed tissue received within the end effector.

FIGS. 6-11 illustrate use of the stapling device 100 during a pull through LAR procedure. As shown in FIG. 6, during a pull through LAR procedure, the colon "C" is prolapsed by inverting the colon "C" and pulling the colon "C" through the anus "A". Once the colon "C" is prolapsed, the inverted portion of the colon "C" is positioned through an opening 152 defined by the anvil plate 116 and the centering cone 150 is inserted into a lumen "L" of the colon "C" such that the inverted portion of the colon "C" is positioned about the distal portion of the shell housing 126 of the shell assembly 108 (FIG. 6A) radially inward of the anvil rods 118.

Figure 8:
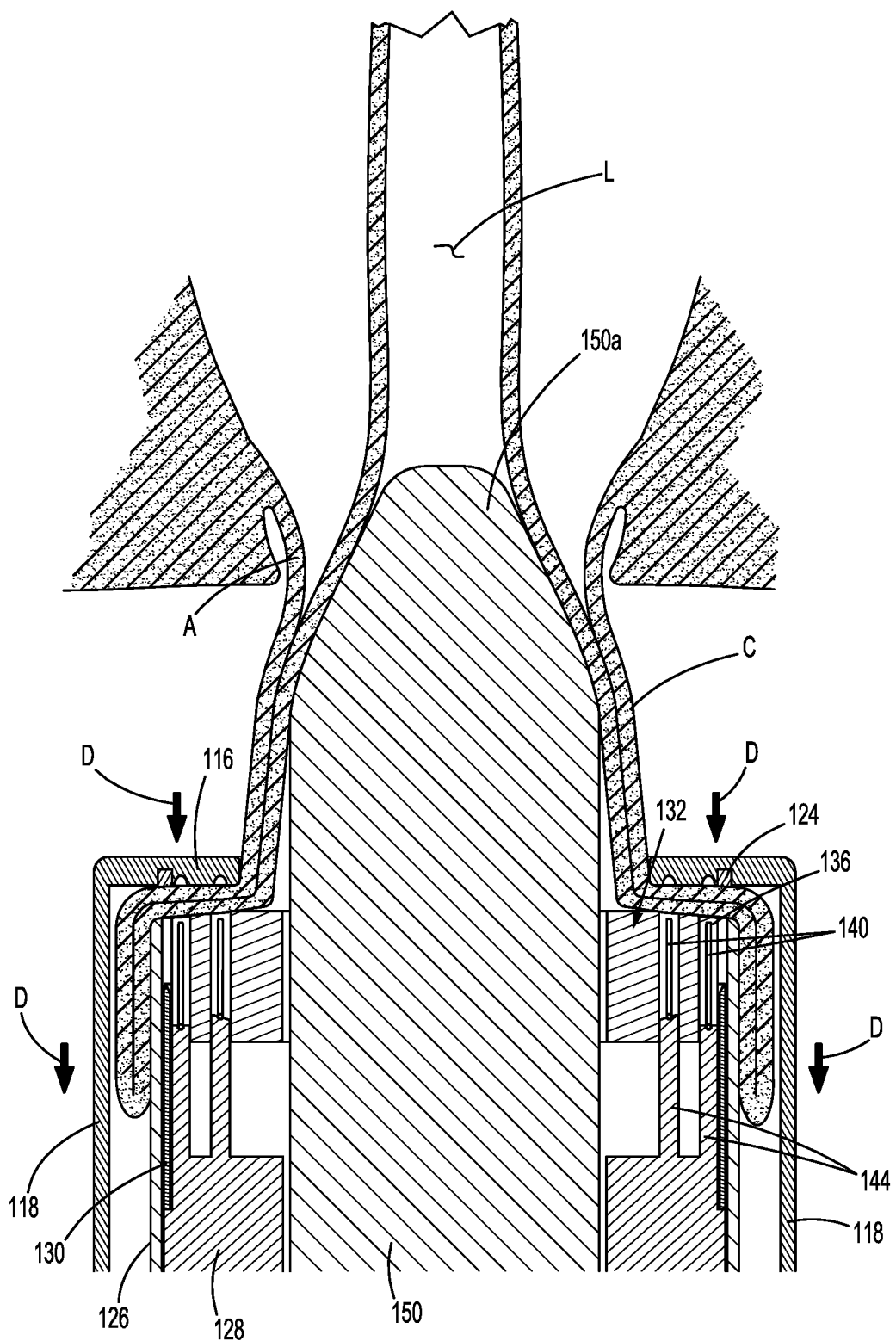
FIG. 8 is a cross-sectional view taken through the end effector shown in FIG. 7 with the anvil assembly in the clamped position.

FIGS. 7 and 8 illustrate end effector 106 of the stapling device 100 (FIG. 1) as the anvil assembly 110 is moved in the direction indicated by arrows "D" from the open position to the clamped position. When the anvil assembly 110 is moved to the clamped position, the anvil plate 116 clamps the inverted portion of the colon "C" against the staple cartridge 132. As illustrated, in this position (FIG. 8), the knife blade 130 is positioned radially outward of the staple cartridge 132 and is aligned with the cut ring 124 on the anvil plate 116.

Figure 9:
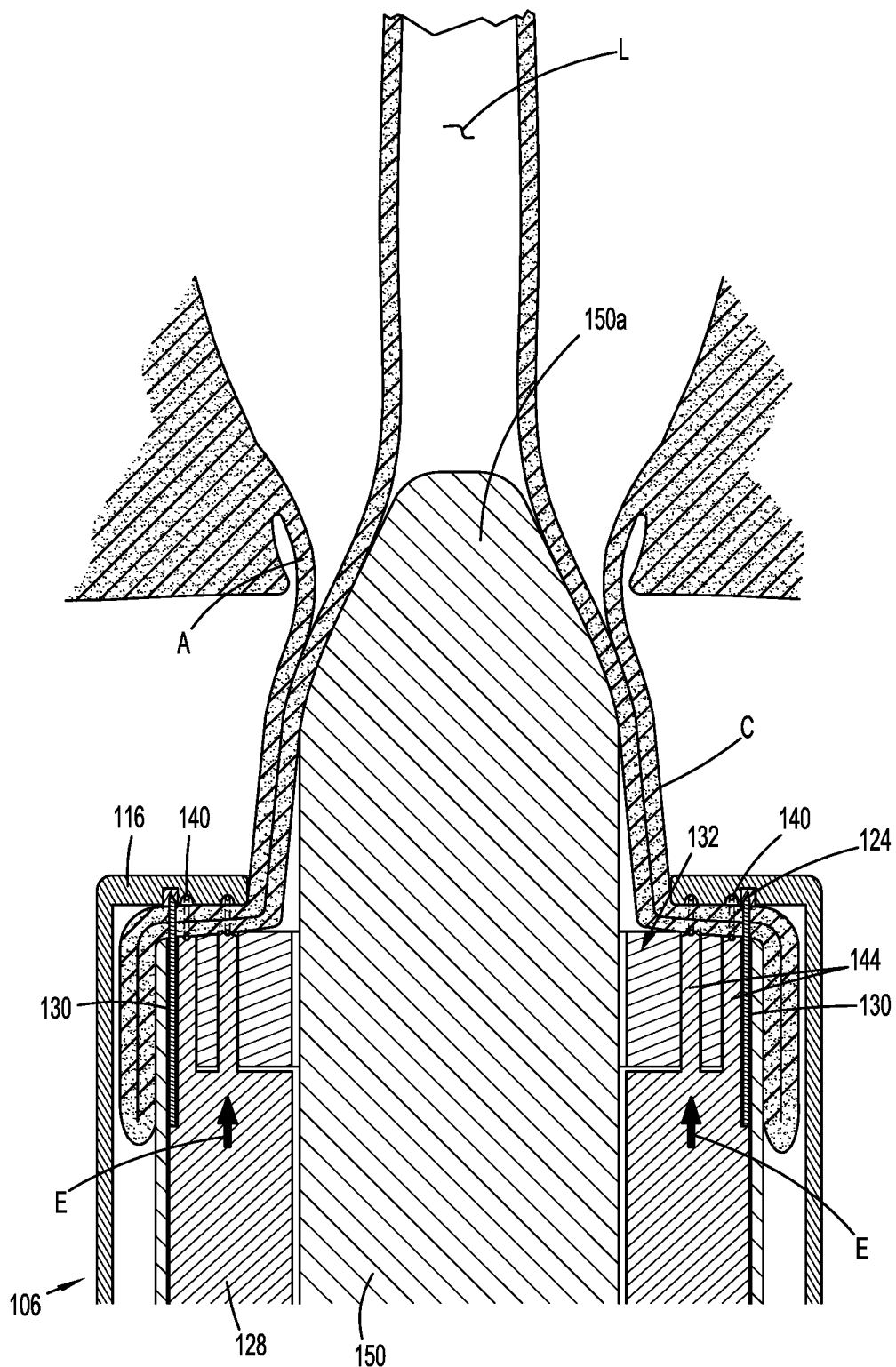
FIG. 9 is a cross-sectional view taken through the end effector shown in FIG. 8 with the anvil assembly in the clamped position as the surgical stapling device is fired.
Figure 10:
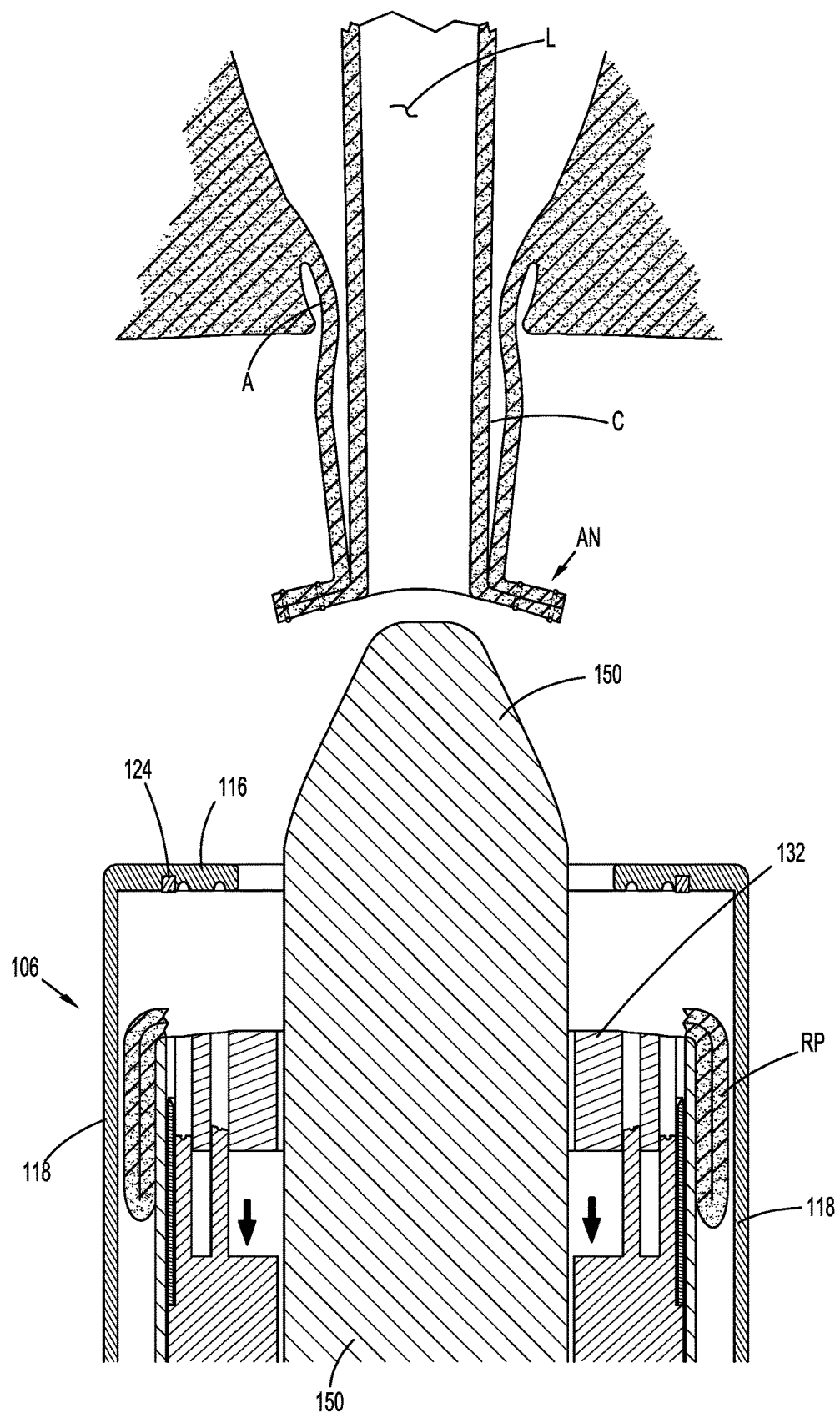
FIG. 10 is a side cross-sectional view of the end effector shown in FIG. 9 after firing of the surgical stapling device with the end effector removed from within the prolapsed tissue.

FIG. 9 illustrates end effector 106 of the stapling device 100 (FIG. 1) as the stapling device 100 is fired by actuating the firing trigger 112 (FIG. 1). When the firing trigger 112 is actuated, the pusher 128 and the knife blade 130 are moved in the direction of arrows "E" from their retracted positions to their advanced positions to eject the staples 140 from the staple cartridge 132 and advance the knife blade 130 into the inverted portion of the colon "C" clamped between the anvil plate 116 and the staple cartridge 132. These actions staple the inverted portions of the colon "C" and cut the tissue in the path of the knife blade 130 radially outward of the staple cartridge 132. After the stapling device 100 (FIG. 1) is fired, the end effector 106 of the stapling device 100 can be withdrawn from the lumen "L" of the colon "C" as illustrated in FIG. 10 and the anastomosis "AN" can be visually inspected to ensure that there is no leakage. The anastomosis may also be analyzed using, e.g., indocyanine green fluorescence imaging, to confirm that there is adequate blood flow. It is noted that the resected portion "RP" of the inverted portion of the colon "C" remains about the shell housing 126 and is confined by the anvil rods 118.

Figure 11:
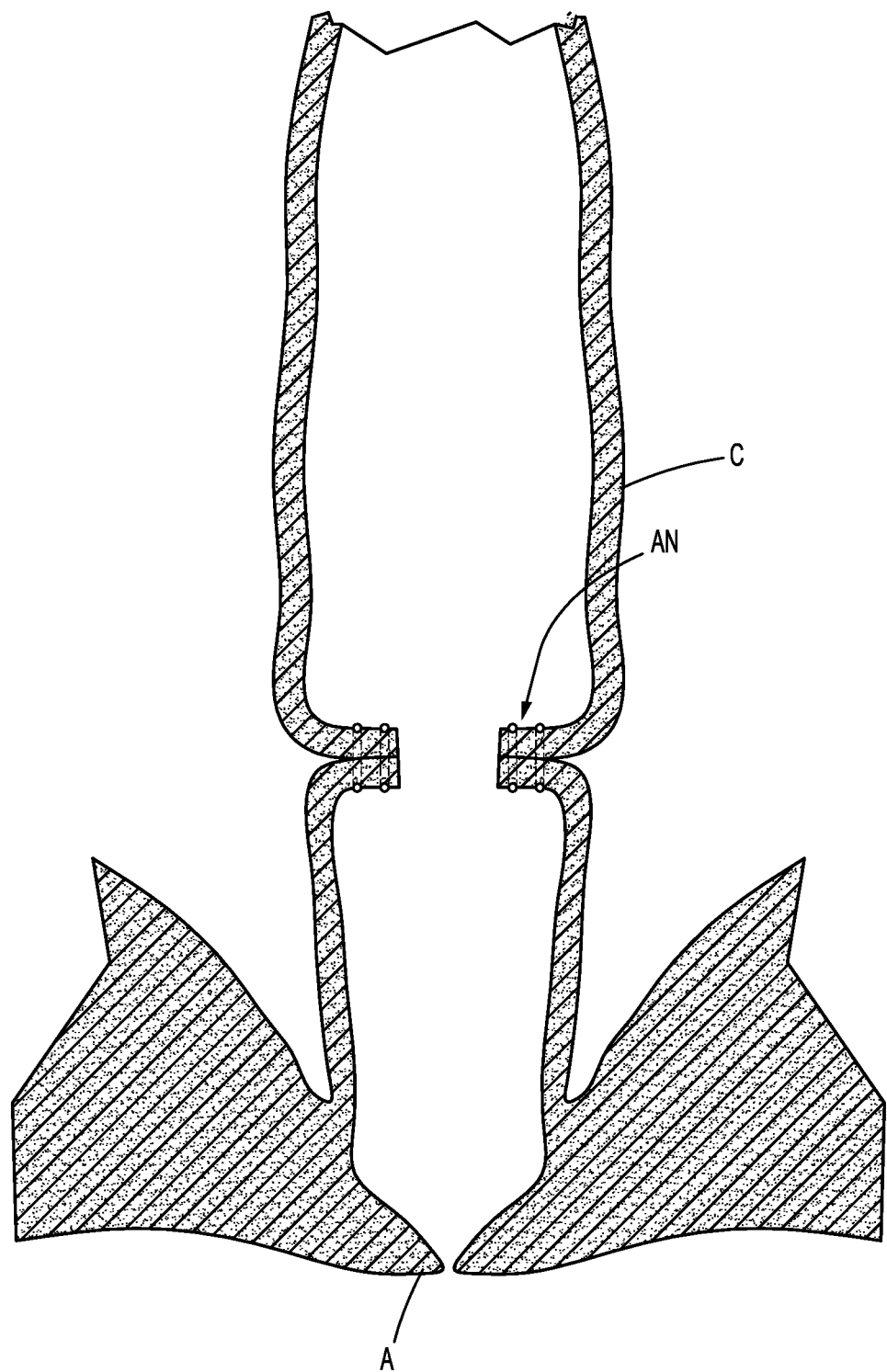
FIG. 11 is a side cross-sectional view of the prolapsed tissue after the prolapsed tissue has been anastomosed and returned to a position within a body cavity.

As illustrated in FIG. 11, once the anastomosis "AN" has been inspected, the inverted portion of the colon "C" can be pushed through the anus "A" back into abdominal cavity.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A surgical stapling device comprising:
    a handle assembly including a firing trigger and an approximation knob;
    an elongate body having a proximal portion and a distal portion, the proximal portion coupled to the handle assembly; and
    an end effector coupled to the distal portion of the elongate body, the end effector including an anvil assembly and a shell assembly, the anvil assembly including an anvil plate and anvil rods that extend proximally from the anvil plate and are positioned about the shell assembly, the anvil plate having a proximally facing surface that defines staple forming pockets, the shell assembly including a shell housing defining a cavity, an annular pusher that is movable within the cavity from a retracted position to an advanced position, an annular staple cartridge, and an annular knife blade, the staple cartridge including staple receiving pockets that receive staples, the knife blade being secured to the pusher radially outwardly of the staple receiving pockets.

2. The surgical stapling device of claim 1, wherein the anvil plate has an annular configuration and defines an opening.

3. The surgical stapling device of claim 1, wherein the shell assembly includes a centering cone that is received within the cavity of the shell housing and extends distally of the staple cartridge.

4. The surgical stapling device of claim 3, wherein the centering cone has a blunt distal end.

5. The surgical stapling device of claim 1, wherein the annular pusher includes fingers that are received within the staple receiving pockets of the staple cartridge such that movement of the annular pusher ejects the staples from the staple receiving pockets.

6. The surgical stapling device of claim 1, wherein the anvil assembly includes four anvil rods.

7. The surgical stapling device of claim 6, wherein the anvil rods are spaced evenly about the anvil plate.

8. An end effector comprising:
   an anvil assembly including an anvil plate and anvil rods that extend proximally from the anvil plate, the anvil plate having a proximally facing surface that defines staple forming pockets; and
   a shell assembly including a shell housing defining a cavity, an annular pusher that is movable within the cavity from a retracted position to an advanced position, an annular staple cartridge, and an annular knife blade, the staple cartridge defining staple receiving pockets that receive staples, the knife blade being secured to the pusher radially outwardly of the staple receiving pockets;
   wherein the anvil rods are positioned about the shell assembly.

9. The end effector of claim 8, wherein the anvil plate has an annular configuration and defines an opening.

10. The end effector of claim 8, wherein the shell assembly includes a centering cone that is received within the cavity of the shell housing and extends distally of the staple cartridge.

11. The end effector of claim 10, wherein the centering cone has a blunt distal end.

12. The end effector of claim 8, wherein the annular pusher includes fingers that are received within the staple receiving pockets of the staple cartridge such that movement of the annular pusher ejects the staples from the staple receiving pockets.

13. The end effector of claim 8, wherein the anvil assembly includes four anvil rods.

14. The end effector of claim 13, wherein the anvil rods are spaced evenly about the anvil plate.

15. A surgical stapling device comprising:
   an elongate body having a proximal portion and a distal portion; and
   an end effector coupled to the distal portion of the elongate body, the end effector including an anvil assembly and a shell assembly, the anvil assembly including an anvil plate and anvil rods that extend proximally from the anvil plate and are positioned about the shell assembly, the anvil plate having a proximally facing surface that defines staple forming pockets, the shell assembly including a shell housing defining a cavity, an annular pusher that is movable within the cavity from a retracted position to an advanced position, an annular staple cartridge, and an annular knife blade, the staple cartridge including staple receiving pockets that receive staples, the knife blade being secured to the pusher radially outwardly of the staple receiving pockets;
   wherein the shell assembly includes a centering cone that is received within the cavity of the shell housing and extends distally of the staple cartridge.

16. The surgical stapling device of claim 15, wherein the anvil plate has an annular configuration and defines an opening.

17. The surgical stapling device of claim 15, wherein the centering cone has a blunt distal end.

18. The surgical stapling device of claim 15, wherein the annular pusher includes fingers that are received within the staple receiving pockets of the staple cartridge such that movement of the annular pusher ejects the staples from the staple receiving pockets.

19. The surgical stapling device of claim 15, wherein the anvil assembly includes four anvil rods.

20. The surgical stapling device of claim 19, wherein the anvil rods are spaced evenly about the anvil plate.

* * * * *